United States Patent [19]

Micetich et al.

[11] 4,172,078

[45] Oct. 23, 1979

[54] THIAZOLINEAZETIDINONE DERIVATIVES

[75] Inventors: Ronald G. Micetich, Sherwood Park; Chia-Cheng Shaw; Peter K. Wolfert, both of Edmonton, all of Canada

[73] Assignee: Connlab Holdings Limited, Canada

[21] Appl. No.: 860,857

[22] Filed: Dec. 15, 1977

[30] Foreign Application Priority Data

Dec. 31, 1976 [GB] United Kingdom ............... 54408/76

[51] Int. Cl.² .......................................... C07D 277/08
[52] U.S. Cl. .................................. 265/245.4; 424/246; 260/239.1; 424/271
[58] Field of Search .................................. 260/306.7 R

[56] References Cited

U.S. PATENT DOCUMENTS

| | | | |
|---|---|---|---|
| 3,862,164 | 1/1975 | Cooper | 260/306.7 |
| 3,880,872 | 4/1975 | Kukolja et al. | 260/306.7 C |
| 3,989,685 | 11/1976 | Tanida et al. | 260/239.1 |
| 4,009,159 | 2/1977 | Kamiya et al. | 260/239.1 |
| 4,052,408 | 10/1977 | Hensler et al. | 260/306.7 C |
| 4,077,970 | 3/1978 | Foglio et al. | 260/306.7 C |

FOREIGN PATENT DOCUMENTS 829304 11/1975 Belgium .
830089 12/1975 Belgium .
832424 2/1976 Belgium .

OTHER PUBLICATIONS

Flynn, Cephalosporins and Penicillins, pp. 199–203 (1972).
Tetrahedron Letters No. 13, pp. 975–978 (1976).
Franceschi, JACS, vol. 99, Jan. 9, 1977, pp. 248–250.

*Primary Examiner*—Nicholas S. Rizzo
*Attorney, Agent, or Firm*—Cushman, Darby & Cushman

[57] ABSTRACT

Thiazolineazetidinone derivatives of the formulae 1,2, and 3.

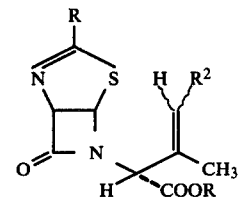

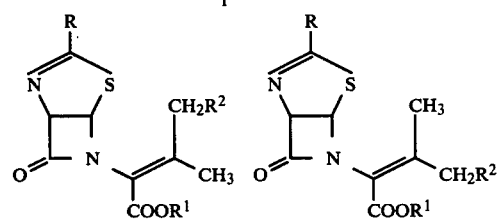

wherein R is derived from the commonly known carboxamido groups present in penicillins, $R^1$ is a carboxy protecting group commonly used in penicillin chemistry, and $R^2$ is Cl, Br, I, CN, lower alkoxy, lower acyloxy, SCN, $SCH_3$, S-phenyl, S-heteroaryl such as 5-mercaptotetrazole or 2-mercapto-5-methyl-1,3,4-thiadiazole, $NO_3$, $N_3$, NH-phenyl, and $N(CH_3)_2$ with the proviso that $R^2$ in the compounds of formula 1 is limited to Cl, Br, I, and lower acyloxy, and a process for preparing said compounds from 2-(substituted methyl) penicillin sulfoxides followed by treatment with a base.

The compounds of formulae 1,2, and 3 are useful as intermediates in the synthesis of cephalosporins.

7 Claims, No Drawings

THIAZOLINEAZETIDINONE DERIVATIVES

This invention relates to new compounds of the formula 1, and to the process for the preparation of compounds of formula 1 and of the related compounds of formulae 2 and 3

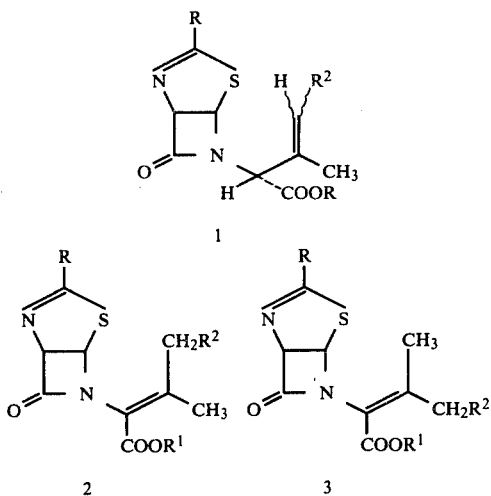

wherein R is derived from the carboxamido group of commonly known penicillins and is selected from the group consisting of H; $C_1$–$C_4$ alkoxy, phenoxy and benzyloxy; $C_1$–$C_8$ alkyl, optionally substituted with hydroxy, mercapto, $C_1$–$C_4$ alkoxy, $C_1$–$C_4$ alkylthio, or cyano, phenyl, optionally substituted in the o-, m-, or p-positions by F, Cl, Br, I. $CH_3$, $OCH_3$, and $NO_2$; benzyl, α-phenylethyl, α-phenyl-α-methylethyl, phenoxymethyl, α-phenoxyethyl and thiophenoxymethyl; heteroarylmethyl such as tetrazol(1-, 2-, 5-)yl-methyl, and thien-2-ylmethyl; heteroaryl such as 3-phenyl-5-methylisoxazolyl; $R^1$ is a carboxy protecting group commonly used in penicillin chemistry and is selected from the group consisting of $C_1$–$C_6$ alkyl, $C_4$–$C_6$ t-alkyl, benzyl (optionally substituted in the phenyl ring by $OCH_3$, Cl, $CH_3$, or $NO_2$), benzhydryl, methoxymethyl, phenoxymethyl, benzyloxymethyl, trityl, trimethylsilyl, phthalimidomethyl, phthalidyl or trichloroethyl; and $R^2$ is selected from the group consisting of halogens having an atomic weight greater than 19, lower alkoxy, lower acyloxy, lower alkylthio, cyano, thiocyano, thiophenyl, 5-heteroaryl containing from 1-3 carbon atoms and from 2-4 hetero atoms such as 5-mercaptotetrazolyl or 2-mercapto-5-methyl 1,3,4-thiadiazolyl, nitro, azido, phenylamino, and di(lower alkyl)amino, with the proviso that the term "lower" represents the presence of 1-3 carbon atoms and that the significance of $R^2$ in the compounds of formula 1 is limited to halogen with an atomic weight greater than 19 and to lower acyloxy.

The nature of the groups R and $R^1$ is not important for the purposes of this invention, and many examples of such groups are found in the literature, e.g. in Tanida et al. U.S. Pat. No. 3,989,685, issued Nov. 2, 1976 or in Kamiya et al. U.S. Pat. No. 4,009,159, issued Feb. 22, 1977.

BACKGROUND OF THE INVENTION

Compounds of the formulae 1, 2, and 3 in which $R^2$ is hydrogen have been described by a number of authors, and a comprehensive review of the early work in this field may be found in "Cephalosporins and Penicillins", E. H. Flynn, Ed., Academic Press, New York and London 1972, p. 199 ff. Those latter compounds were initially obtained by treating a penicillin sulfoxide with a trialkylphosphite to obtain the corresponding compounds of formula 1 which, upon treatment with triethylamine, yielded the corresponding compounds of formulae 2 or 3. Micetich et al., Tetrahedron Letters 1976, 975 found that heating of certain 6-thioamides of penicillin sulfoxides gave the corresponding dithiazineazetidinones which yielded the corresponding compounds of formula 1 in which $R^2$ is hydrogen upon exposure to light, moisture, and air. Similar compounds of formula 1 have also been obtained by Kukolja et al., U.S. Pat. No. 3,880,872, issued Apr. 29, 1975, by treating certain 4-chloroazetidinone-3-imidoylchlorides with metal sulfides. Franceschi et al., J. Am. Chem. Soc. 99,248(1977), treated certain compounds of formula 1 in which $R^2$ is hydrogen with N-bromosuccinimide to obtain the corresponding compounds of formulae 2 and 3 in which $R^2$ is bromine, converted them to the corresponding compounds in which $R^2$ is acetoxy or methoxy which were obtained as mixtures of E+Z isomers, separated the latter compounds by chromatography, and cyclized them to mixtures of the correspondingly substituted $\Delta^2$- and $\Delta^3$-cephems by multistage procedures. The above processes are described in detail in Belgian Pat. Nos. 829,304, published Nov. 21, 1975; 830,089, published Dec. 11, 1975; and 832,424, published Feb. 16, 1976.

SUMMARY DESCRIPTION OF THE INVENTION

The novel compounds of formula 1 in which R and $R^1$ are as defined above and $R^2$ is Cl, Br, I, or lower acyloxy are prepared as follows.

A 2-(substituted methyl) penicillin sulfoxide of formula 4 in which R and $R^1$ are as defined above and $R^2$ is Cl, Br, I, or lower acyloxy is treated in solution in an inert solvent with at least one molar equivalent of a tri(lower alkyl) phosphite, or in solution in a very large molar excess of a tri(lower alkyl) phosphite in the absence of a solvent. Cooling, washing, and evaporating the reaction mixture gives almost exclusively the corresponding compounds of formula 1 which may be regarded as substituted vinylic thiazolineazetidinones.

Said last-named compounds are treated with an organic base to give the corresponding substituted allylic thiazolineazetidinone derivatives of formula 2 in which R and $R^1$ are as defined above and $R^2$ is Cl, Br, I, or lower acyloxy. It is a particular advantage of the process of this invention that the above reaction gives again almost exclusively only the compounds of formula 2 in which the group $CH_2R^2$ is trans to the carboxylic ester group $COOR^1$, so that purification e.g. by chromatography is not required.

When it is desired to obtain compounds of formula 3, a compound of formula 2 in which R and $R^1$ are as defined above and $R^2$ is Cl, Br, or I is reacted with a nucleophilic reagent in the conventional manner. However, replacement of the group $R^2$ in a compound of formula 2 by another group $R^2$ as defined in the first instance results in inversion of the geometric configuration, so that the appropriate compound of formula 3 is obtained in which the group $CH_2R^2$ is cis to the carboxylic ester group $COOR^1$. Said compounds of formula 3 are obtained in this manner almost exclusively, with no more than a trace of the corresponding compound of formula 2 being present in the reaction mixture.

The compounds of formula 2 and 3 obtained as described above are useful as intermediates in the synthesis of substituted cephem derivatives which are known to possess antibiotic activities, as described e.g. in Belgian Pat. Nos. 829,304, 830,089, and 832,424, and in Franceschi et al., all cited above.

DETAIL DESCRIPTION OF THE INVENTION

The starting material for the preparation of the compounds of formulae 1, 2, and 3 is a 2-(substituted methyl) penicillin sulfoxide of formula 4 in which R and $R^1$ are as defined in the first instance and $R^2$ is Cl, Br, I, or lower acyloxy. Such starting materials are prepared according to the method described in German Offenlegungsschrift No. 2,352,199, published May 2, 1974. Such compounds of formula 4 exist in a number of forms, and we have found it particularly advantageous to use the 2$\beta$-(substituted methyl) - 2$\alpha$-methylpenam-1$\beta$-sulfoxides as starting materials.

Said starting material of formula 4 in which R and $R^1$ are as defined above and $R^2$ is Cl, Br, I, or lower acyloxy is dissolved in an inert solvent and heated in the presence of at least one molar equivalent of a tri(lower alkyl)phosphite. Suitable inert solvents are monocyclic aromatic hydrocarbons such as benzene, toluene, or xylene, with toluene being preferred; ethers such as di(lower alkoxy) (lower alkanes), with dimethoxyethane being preferred; and cyclic ethers such as dioxane. The temperature of the reaction is held within the range of 60°–150° C., preferably within the range of 100°–120° C., and the duration of the reaction is from 1–8 hours, preferably 2–6 hours. Trimethylphosphite is the preferred reagent and is used in quantities ranging from 1–3 molar equivalents, preferably about 2 molar equivalents.

Alternatively, the reaction may also be conducted in the absence of a solvent using a large molar excess of the tri(lower alkyl) phosphite, e.g. trimethylphosphite, both as reagent and as solvent.

The progress of the reaction may be followed by thin layer chromatography, and cooling the reaction mixture, washing with water, drying, and evaporating yields the corresponding compound of formula 1 in which R and $R^1$ are as defined above and $R^2$ is Cl, Br, I. or lower acyloxy.

Said last-named compounds of formula 1 are dissolved in an inert solvent and treated with 1–5 molar equivalents, preferably about 2 molar equivalents of an oranic base at a temperature within the range of from −30° C. to 30° C., preferably within the range of −10° C. to 20° C., for periods of time within the range of 5–120 minutes, preferably for 30–60 minutes. Suitable inert solvents include halogenated hydrocarbons containing from 1–3 carbon atoms and from 2–4 halogen atoms, ethers such as diethyl ether or di(lower alkoxy)(lower alkanes), e.g. dimethoxyethane, and cyclic ethers such as tetrahydrofuran, with the halogenated hydrocarbons as defined above being preferred. Suitable organic bases include the tri(lower alkyl)amines, pyridine, picoline, collidine, aniline, and dimethylaniline, with the tri(lower alkyl)amines being preferred. The reaction is terminated by adding the reaction mixture to a large molar excess of a cold, dilute mineral acid, preferably to ice-cold 10% hydrochloric acid, separating the organic from the aqueous phase, extracting the aqueous phase with a halogenated hydrocarbon solvent as defined above, combining the extracts with the organic phase, washing with water or brine, drying, and evaporating, to obtain the corresponding compound of formula 2 in which R and $R^1$ are as defined above and $R^2$ is Cl, Br, I, or lower acyloxy. The pmr spectrum of those compounds of formula 2 shows that they are thus obtained almost exclusively in the form in which the group $CH_2R^2$ is trans to the carboxylic ester group $COOR^1$.

The above compounds of formula 2 in which R and $R^1$ are as defined above and $R^2$ is Cl, Br, or I are easily transformed to the appropriate compounds of formula 3 in which $R^2$ has one of the other definitions listed above, i.e. lower alkoxy, lower acyloxy, lower alkylthio, cyano, thiocyano, thiophenyl, 5-mercaptotetrazolyl, 2-mercapto-5-methyl-1,3,4-thiadiazolyl, nitro, azido, phenylamino, or di(lower alkyl)amino, in the conventional manner, by reaction with a nucleophilic agent selected from sodium or lithium lower alkoxides; sodium, lithium, or tetramethylguanidinium formate, acetate, or propionate; the sodio or lithio salts of lower alkylthiols; silver cyanide; potassium or lead thiocyanide; the sodio or lithio salts of thiophenyl, of 5-mercaptotetrazole, or of 2-mercapto-5-methyl-1,3,4-thiadiazole; silver nitrate; sodium or tetramethylguanidinium azide; aniline; and di(lower alkyl)amines, respectively. The reaction with the appropriate nucleophilic agent is carried out by dissolving the compound of formula 2 in which R and $R^1$ are defined above and $R^2$ is Cl, Br, or I in an inert solvent as defined above, adding 1–10 molar equivalents of the nucleophilic agent, preferably about 2–5 molar equivalents, and agitating the mixture at a temperature within the range of from −10° C. to 40° C., preferably within the range of from 0°–30° C., for periods of time of from 2–24 hours. The choice of the inert solvent will depend upon the nature of the nucleophilic agent. Thus, when using a tetramethylguanidinium salt or aniline or a di(lower alkyl)amine as the nucleophilic agent the preferred solvent is a halogenated hydrocarbon as defined above; when using a lithium, sodium, potassium, lead, or silver derivative as the nucleophilic agent it is preferred to use dimethoxyethane or tetrahydrofuran as the solvent, and in the latter case a water-immiscible solvent such as a halogenated hydrocarbon as defined above is added to the reaction mixture after completion of the reaction. Filtering, washing with water or with brine, drying, and evaporating yields the appropriate compound of formula 3 in which R and $R^1$ are as defined above, $R^2$ is the substituent introduced by the nucleophilic agent, i.e. lower alkoxy, formyloxy, acetoxy, propionyloxy, lower alkylthio, cyano, thiocyano, phenylthio, 5-mercaptotetrazolyl, 2-mercapto-5-methyl-1,3,4-thiodiazolyl, nitro, azido, phenylamino, and di(lower alkyl)amino, respectively, and the group $CH_2R^2$ is cis to the carboxylic ester group $COOR^1$.

The following formulae and Examples will illustrate the invention without limiting its scope.

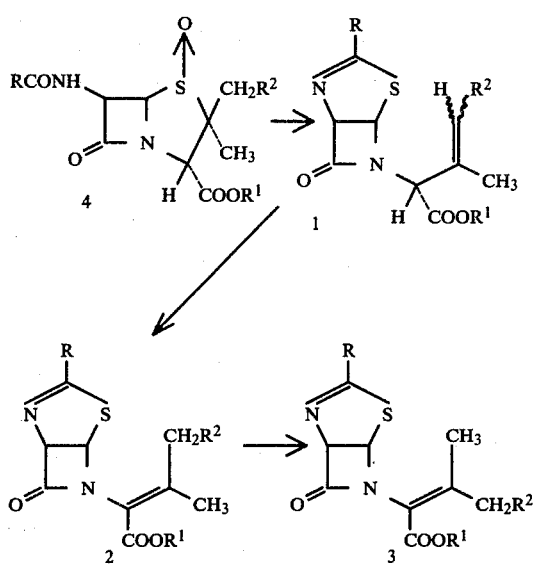

EXAMPLE 1 p-Nitrobenzyl 3-Phenoxymethyl-1α,5α-4-thia-2,6-diazabicyclo(3.2.0)-2-Heptene-6-(1′-chlorovinylethyl)Acetate-7-one (1, R=C₆H₅OCH₂, R¹=p-C₆H₄NO₂, R²=Cl)

A stirred solution of p-nitrobenzyl 6-phenoxyacetamido-2β-chloromethyl-2α-methylpenam-1β-sulfoxide-3-carboxylate (4, R=C₆H₅OCH₂, R¹=p-C₆H₄NO₂, R²=Cl, 107 mg, 0.2 mmoles) and trimethyl phosphite (50 mg., 0.4 mmole) in toluene (2 ml), was heated under reflux in an oil-bath maintained at 110°–120° C. for 6 hrs (by which time the reaction was complete from thin layer chromatography). The reaction mixture was cooled, washed with water, dried (MgSO₄), filtered and concentrated to give 60 mg. of an oil. The ir spectrum and pmr (CDCl₃) spectrum: δ1.85 (s, 3H, C$\underline{H}_3$), 4.97 (d, 3H, —OC$\underline{H}_2$— and —C$\underline{H}$-COOC$\underline{H}_2$φ-NO₂), 5.34 (s, 2H, COOC$\underline{H}_2$φNO₂), 5.9 to 6.1 (m, 3H, β-lactam protons and vinylic H), 6.85 to 7.58 (m, 7H, C₆H₄ and 2H from p-C₆H₄NO₂), 8.28 (d, 2H, from p-C₆H₄NO₂) were in agreement with the assigned structure.

EXAMPLE 2

Benzhydryl 3-Phenoxymethyl-1α,5α-4-thia-2,6-Diazabicyclo(3.2.0)-2-Heptene-6-(1′-chlorovinylethyl)Acetate-7-one, (1, R=C₆H₅OCH₂, R¹=CH(C₆H₅)₂, R²=Cl)

A stirred solution of benzhydryl 6-phenoxyacetamido-2β-chloromethyl-2α-methylpenam-1β-sulfoxide-3-carboxylate (4, R=C₆H₅OCH₂, R¹=CH(C₆H₅)₂, R²=Cl, 114 mg., 0.2 mmoles) and trimethylphosphite (50 mg., 0.4 mmoles) in toluene (2 ml) was heated under reflux in an oil-bath maintained at 110°–120° C. for 2.5 hrs (by which time the reaction was complete from thin layer chromatography). The reaction mixture was washed well (4x) with water, dried (MgSO₄), filtered and concentrated to a pale yellow sticky foam (0.12 g.). The foam was dissolved in ether and the title compound precipitated as a white solid (0.1 g) by adding hexane at −75° C. The pmr (CDCl₃) spectrum δ1.72 (s, 3H, C$\underline{H}_3$), 4.87 (s, 2H, OC$\underline{H}_2$—), 5.0 (s, 1H, C$\underline{H}$COOR), 5.90 (m, 3H, β-lactam protons and vinylic H), 6.82 to 7.4 (m, 16H, aryl C₆$\underline{H}_5$ and C$\underline{H}$φ₂), is in agreement with the assigned structure.

EXAMPLE 3

Benzhydryl 3-Phenoxymethyl-1α,5α,4-Thia-2,6-Diazabicyclo(3.2.0)-2-Heptene-6-bromovinylethyl)Acetate-7-One, (1, R=C₆H₅OCH₂, R¹=CH(C₆H₅)₂, R²=Br)

A stirred solution of benzhydryl 6-phenoxyacetamido-2β-bromoethyl-2α-methylpenam-1β-sulfoxide-3-carboxylate (4, R=C₆H₅OCH₂, R¹=CH(C₆H₅)₂, R²=Br, 122 mg., 0.2 mmole), and trimethyl phosphite (50 mg., 0.4 mmole) in toluene (2 ml), was heated under reflux in an oil-bath maintained at 110°–120° C. for 2.5 hrs. Work up as described in Example 2 gave 0.11 g. of a yellow solid. Precipitation of the compound in an ether solution by hexane at −75° C. gave 0.1 g. of a white solid. The pmr (CDCl₃) spectrum: δ1.7 (s, 3H, C$\underline{H}_3$), 4.8 (s, 2H, OC$\underline{H}_2$), 5.0 (s, 1H, C$\underline{H}$COOR), 5.8 (m, 2H, β-lactam protons), 6.03 (s, 1H, vinylic H), 6.8 to 7.35 (m, 16H, aryl C₆$\underline{H}_5$ and C$\underline{H}$φ₂) is in agreement with the structure.

EXAMPLE 4

Benzhydryl 3-Phenoxymethyl-1α,5α,4-Thia-2,6-Diazabicyclo(3.2.0)-2-Heptene-6-(1′-iodovinylethyl)Acetate-7-One, (1, R=C₆H₅OCH₂, R¹=CH(C₆H₅)₂, R²=I)

A stirred solution of benhydryl 6-phenoxyacetamido-2β-iodomethyl-2α-methylpenam-1β-sulfoxide-3-carboxylate (4, R=C₆H₅ICH₂, R¹=CH(C₆H₅)₂, R²=I, 5 g., 7.6 mmole), and trimethyl phosphite (1.9 g., 15.2 mmoles) in toluene (95 ml), was heated under reflux in an oil-bath maintained at 110°–120° C. for 2.5 hrs (by which time the reaction was complete by thin layer chromatography). The reaction mixture was washed well with water (6x), dried (MgSO₄), filtered and concentrated to give 4.6 g., of a white solid. The product was stirred with a small amount of ether, filtered and dried to give 2.6 g., of a white solid m.p. 148°–150° C. The pmr (CDCl₃) spectrum: δ1.78 (s, 3H, C$\underline{H}_3$), 4.8 (s, 2H, OC$\underline{H}_2$), 5.1 (s, 1H, C$\underline{H}$COOR), 5.85 (m, 2H, β-lactam protons), 6.18 (s, 1H, vinylic proton), 6.8 to 7.45 (m, 16H, aryl C₆$\underline{H}_5$ and C$\underline{H}$φ₂); and in benzene d₆ - δ1.1 (s, 3H, C$\underline{H}_3$), 3.8 (d, 2H, OC$\underline{H}_2$), 4.3 (s, 1H, C$\underline{H}$COOR), 4.68 and 4.83 (d, m, 2H, β-lactam protons), 5.45 (s, 1H, vinylic proton), 6.1 to 6.6 (m, 16H, aryl C₆H₅ and C$\underline{H}$φ₂) are in agreement with the assigned structure.

EXAMPLE 5

2,2,2-Trichloroethyl 3-Phenoxymethyl-1α,5α,4-Thia-2,6-Diazabicyclo(3.2.0)-2-Heptene-6-(1′-iodovinylethyl)Acetate-7-One (1, R=C₆H₅OCH₂, R¹=CH₂CCl₃, R²=I)

2,2,2-Trichloroethyl 6-phenoxyacetamido-2β-iodomethyl-2α-methylpenam-1β-sulfoxide-3-carboxylate (4, R=C₆H₅OCH₂, R¹=CH₂CCl₃, R²=I, 1 g., 1.61 mmole) was heated with trimethylphosphite (400 mg., 3.22 mmole) in toluene (20 ml) for 2 hrs and the product worked up as described in Example 4, to give 400 mg., of the title compound as a white powder, m.p. 125°–127° C. The pmr (acetone d₆) spectrum: δ1.4 (s, 3H, C$\underline{H}_3$), 4.48 (m, 4H, —OC$\underline{H}_3$ and C$\underline{H}_2$CCl₃), 4.75 (s, 1H, C$\underline{H}$COOCH₂CCl₃), 5.52 and 5.68 (m, s, 2H, β-lactam protons), 6.25 (s, 1H, vinylic proton), 6.4 to 6.9 (m, 5H, C₆$\underline{H}_5$) is characteristic of the compound.

EXAMPLE 6

Methyl 3-Phenoxymethyl-1α,5α,4-Thia-2,6-Diazabicyclo(3.2.0)-2-Heptene-6-(1'-acetoxyvinylethyl)Acetate-7-One, (1, R=C$_6$H$_5$OCH$_2$, R$^1$=CH$_3$, R$^2$=OCOCH$_3$)

A solution of methyl 6-phenoxyacetamido-2β-acetoxymethyl-2α-methylpenam-1β-sulfoxide-3-carboxylate (4, R=C$_6$H$_5$OCH$_2$, R$^1$=CH$_3$, R$^2$=OCOCH$_3$), 0.44 g., 1 mmole) and trimethyl phosphite (0.252 g., 2 mmoles) in toluene (10 ml) was stirred and heated under reflux in an oil-bath maintained at 110°–120° C., for 6 hrs and the reaction product worked up as described in Example 3 to give 380 mg., of a yellow foam. A pmr spectrum and tlc on this product indicated the presence of starting material in addition to the desired product. The product was purified by chromatography on silica gel using methylene chloride-ether gradient elution, when 0.25 g., of the desired product was obtained as a white foam. The pmr (CDCl$_3$) spectrum: δ1.7 (s, 3H, CH$_3$), 2.12 (d, 3H, OCOCH$_3$), 3.78 (s, 3H, COOCH$_3$), 4.85 and 4.92 (ss, 3H, —CHCOOCH$_3$ and —OCH$_2$), 5.12 and 5.3 (s, s, 1H, vinylic proton), 5.90 (m, 2H, β-lactam protons), 6.9 to 7.32 (m, 5H, C$_6$H$_5$) is characteristic of this compound.

EXAMPLE 7

Benzhydryl 3-Phenoxymethyl-1α,5α,4-Thia-2,6-Diazabicyclo(3.2.0)-2-Heptene-6-(3'-iodomethylbut-2'-enoate)-7-One, (2, R=C$_6$H$_5$OCH$_2$, R$^1$=CH(C$_6$H$_5$)$_2$, R$^2$=I)

A solution of the vinyl iodide, obtained as described in Ex. 4, (1, R=C$_6$H$_5$OCH$_2$, R$^1$=CH(C$_6$H$_5$)$_2$, R$^2$=I, 1.248 g., 2 mmole) in methylene chloride (10 ml) was cooled in an ice bath for 20 mins and triethylamine (0.4 ml) then added. The mixture was stirred at 0° C. for 40 mins and the resulting solution poured into ice cold 10% hydrochloric acid. The layers were separated and the aqueous layer extracted with methylene chloride (3×50 ml). The combined organic layers were washed with brine, dried (Na$_2$SO$_4$), filtered and concentrated to give 1.285 g., of the title compound as a pale yellow foam. The pmr (CDCl$_3$) spectrum: δ1.9 (s, 3H, CH$_3$), 4.1 and 4.48 (dd, 2H, CH$_2$I), 4.7 (br, s, 2H, OCH$_2$), 4.65 and 5.9 (dd, 2H, β-lactam protons), 6.72 to 7.3 (m, 16H, aryl C$_6$H$_5$ and CHφ$_2$) is in agreement with the assigned structure and indicates that the CH$_2$I group is trans to the ester group COOCH(C$_6$H$_5$)$_2$.

EXAMPLE 8

Benzhydryl 3-Phenoxymethyl-1α,5α,4-Thia-2,6-Diazabicyclo(3.2.0)-2-Heptene-6-(3'-azidomethylbut-2'-enoate)-7-One, (3, R=C$_6$H$_5$OCH$_2$, R$^1$=CH(C$_6$H$_5$)$_2$, R$^2$=N$_3$)

A solution of the allylic iodide obtained as described in Example 7 (2, R=C$_6$H$_5$OCH$_2$, R$^1$=CH(C$_6$H$_5$)$_2$, R$^2$=I, 1.285 g., ~2 mmoles) in methylene chloride (5 mls) was added to an ice cold, stirred, solution of tetramethylguanidinium azide (624 mg., ~4 mmoles) in methylene chloride (7 ml) in a nitrogen atmosphere, and the mixture stirred at 0° for 4 hrs. The resulting pale brown solution was poured into ice-cold brine, shaken, and the layers separated. The aqueous layer was extracted with methylene chloride (3×50 ml). The combined extracts were washed with brine (twice), dried (Na$_2$SO$_4$), filtered and concentrated to give 1.14 g., of the crude product as a pale yellow foam. This product dissolved in benzene was filtered through a short silica gel column, eluted with benzene and then 10% ethylacetate in benzene. Concentration of the eluants gave 895 mg., (83% overall yield) of the purified product as a white foam. The nmr (CDCl$_3$) spectrum δ1.8 (s, 3H, CH$_3$), 4.25 (q, 2H, CH$_2$N$_3$), 4.75 (m, 2H, OCH$_2$), 5.72 and 6.0 (dd, 2H, β-lactam protons), 6.75 to 7.4 (m, 16H, aryl H and CHφ$_2$), is in agreement with the assignment and indicates that the CH$_2$N$_3$ group is cis to the ester group COOCH(C$_6$H$_5$)$_2$.

EXAMPLE 9

Benzhydryl 3-Phenoxymethyl-1α,5α,4-Thia-2,6-Diazabicyclo(3.2.0)-2-Heptene-6-(3'-formyloxymethylbut-2-enoate)-7-One, (3, R—C$_6$H$_5$OCH$_2$, R$^1$—CH(C$_6$H$_5$)$_2$, R$^2$—OCOH)

A solution of the allylic iodide, 2 (615 mg., ~1 mmole prepared as described in Example 7) in methylene chloride (4 ml) was added dropwise to a stirred solution of tetramethylguanidinium formate (891 mg., ~5 mmole) in methylene chloride (6 ml) at room temperature, and the mixture stirred at ambient temperature in a nitrogen atmosphere for 15 hrs. The resulting brown solution (tlc shows no starting material) was stirred with ice-water and the layers separated. The aqueous layer was extracted with ethyl acetate (2×50 ml). The combined organic layers were washed with brine (twice), dried (Na$_2$SO$_4$), filtered and concentrated to give 521 mg., of a light brown foam. The crude product dissolved in ethyl acetate was filtered through a short silica gel column and eluted with ethyl acetate. Concentration gave 386 mg., (71% overall yield) of a very light brown foam. The pmr (CDCl$_3$) spectrum: δ1.85 (s, 3H, CH$_3$), 4.8 (d, 2H, OCH$_2$), 5.18 (s, 2H, CH$_2$OCOH), 5.78 and 5.98 (dd, 2H, β-lactam protons), 6.8 to 7.45 (m, 16H, aryl H and CHφ$_2$), and 7.95 (s, 1H, CHO) is in agreement with the assigned structure and indicates that the CH$_2$OCOH group is cis to the ester group COOCH(C$_6$H$_5$)$_2$. The compound on treatment with aqueous acid formed the lactone showing that the geometry is as indicated in formula 3 where the formate group is cis- to the ester group. In addition a singlet at 2.2 indicated the presence of a trace amount of the trans geometric isomer of formula 2.

We claim:

1. A compound of the formula 1

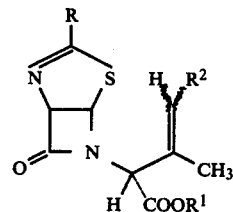

wherein R is selected from the group consisting of H; $C_1$–$C_4$ alkoxy, phenoxy and benzyloxy; $C_1$–$C_8$ alkyl, optionally substituted with hydroxy, mercapto, $C_1$–$C_4$ alkoxy, $C_1$–$C_4$ alkylthio, or cyano, phenyl, optionally substituted in the o-, m-, or p- positions by F, Cl, Br, I. CH$_3$, OCH$_3$, and NO$_2$; benzyl, α-phenylethyl, α-phenyl-α-methylethyl; phenoxymethyl, α-phenoxyethyl, thiophenoxymethyl, tetrazol(1-, 2-, 5-)yl-methyl, thien-2-ylmethyl, and 3-phenyl-5-methylisoxazolyl; R$^1$ is selected from the group consisting of $C_1$–$C_6$ alkyl, $C_4$–$C_6$ t-alkyl, benzyl (optionally substituted in the phenyl ring by $OCH_3$, Cl, $CH_3$, or $NO_2$), benzhydryl, methoxymethyl, phenoxymethyl, benzyloxymethyl, trityl, trimethylsilyl, phthalimidomethyl, phthalidyl and trichloroethyl; and $R^2$ is selected from the group consisting of halogens having an atomic weight greater than 19 and alkanoyloxy of 1–3 carbon atoms.

2. A compound of formula 1 in which R is $C_6H_5OCH_2$, $R^1$ is p-$C_6H_4NO_2$ and $R^2$ is Cl, as claimed in claim 1.

3. A compound of formula 1 in which R is $C_6H_5OCH_2$, $R^1$ is $CH(C_6H_5)_2$ and $R^2$ is Cl, as claimed in claim 1.

4. A compound of formula 1 in which R is $C_6H_5OCH_2$, $R^1$ is $CH(C_6H_5)_2$, and $R^2$ is Br, as claimed in claim 1.

5. A compound of formula 1 in which R is $C_6H_5OCH_2$, $R^1$ is $CH(C_6H_5)_2$ and $R^2$ is I, as claimed in claim 1.

6. A compound of formula 1 in which R is $C_6H_5OCH_2$ $R^1$ is $CH_2CCl_3$, and $R^2$ is I, as claimed in claim 1.

7. A compound of formula 1 in which R is $C_6H_5OCH_2$, $R^1$ is $CH_3$, and $R^2$ is $OCOCH_3$, as claimed in claim 1.

* * * * *